(12) United States Patent
Old

(10) Patent No.: US 7,705,001 B2
(45) Date of Patent: Apr. 27, 2010

(54) THERAPEUTIC SUBSTITUTED GAMMA LACTAMS

(75) Inventor: David W. Old, Irvine, CA (US)

(73) Assignee: Allergan, Inc, Irvine, CA (US)

( * ) Notice: Subject to any disclaimer, the term of this patent is extended or adjusted under 35 U.S.C. 154(b) by 0 days.

(21) Appl. No.: 12/405,684

(22) Filed: Mar. 17, 2009

(65) Prior Publication Data

US 2009/0239867 A1    Sep. 24, 2009

Related U.S. Application Data

(60) Provisional application No. 61/037,626, filed on Mar. 18, 2008.

(51) Int. Cl.
*C07D 207/08* (2006.01)
*C07D 265/30* (2006.01)
*A61K 31/4015* (2006.01)
*A61K 31/5377* (2006.01)

(52) U.S. Cl. .................. 514/237.2; 514/428; 548/572; 544/141

(58) Field of Classification Search .............. 548/141; 544/572; 514/237.2, 428
See application file for complete search history.

(56) References Cited

U.S. PATENT DOCUMENTS

| | | | |
|---|---|---|---|
| 4,166,452 A | 9/1979 | Generales | |
| 4,256,108 A | 3/1981 | Theeuwes | |
| 4,265,874 A | 5/1981 | Bonsen | |
| 6,710,072 B2 | 3/2004 | Burk | |
| 7,091,231 B2 | 8/2006 | Donde | |
| 2003/0149086 A1* | 8/2003 | Cameron et al. ............ | 514/365 |

FOREIGN PATENT DOCUMENTS

WO    WO 94/13295    6/1994

OTHER PUBLICATIONS

U.S. Appl. No. 60/644,069, filed Jan. 14, 2005, Old.
Chourasia, M.K.; Jain, S.K.: Pharmaceutical Approaches to Colon Targeted Drug Delivery Systems. J. Pharm. Pharmaceut Sci 6 (1): 33-66, 2003.
Kotake, Yoshihiko; et al.: Synthesis and Antitumor Activities of Novel 6-5 Fused Ring Heterocycle Antifolates: N-[4-[.omega.-(2-Amino-4-substituted-6,7-dihydrocyclopenta[d]pyrimidin-5-yl)alkyl]benzoyl]-L-glutamic Acids. J. Med. Chem. 1994, 37, 1616-1624.
Remington's Pharmaceutical Sciences, Mack Publishing Company, Easton, Pa., 16th Edition, 1980.
Shareef, M. Ajmal; et al.: Colonic Drug Delivery: An Updated Review. AAPS PharmSci 2003; 5 (2) Article 17.

* cited by examiner

*Primary Examiner*—Kamal A Saeed
*Assistant Examiner*—Michael Barker
(74) *Attorney, Agent, or Firm*—Kevin J. Forrestal; John E. Wurst; Allergan, Inc.

(57) ABSTRACT

Disclosed herein is a compound comprising

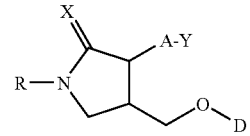

or a pharmaceutically acceptable salt or a prodrug thereof; wherein Y, A, X, R and D are as described.

Methods, compositions, and medicaments related thereto are also disclosed.

13 Claims, No Drawings

THERAPEUTIC SUBSTITUTED GAMMA LACTAMS

RELATED APPLICATION

This application claims the benefit of U.S. Provisional Application Ser. No. 61/037,626, filed Mar. 18, 2008, the disclosure of which is hereby incorporated in its entirety herein by reference.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

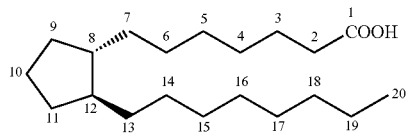

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

In addition to the treatment of glaucoma, prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, baldness, the stimulation of hair growth, and the stimulation of the conversion of vellus hair to terminal hair. The compounds themselves are disclosed below.

DESCRIPTION OF THE INVENTION

Disclosed herein is a compound comprising

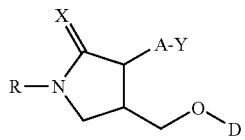

or a pharmaceutically acceptable salt or a prodrug thereof;
wherein
Y is

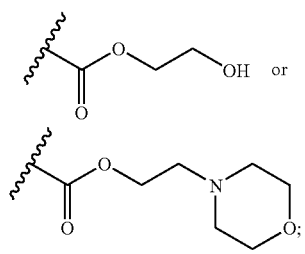

A is —$(CH_2)_6$—, cis —$CH_2CH=CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;
X is S or O;
R is H; or alkyl, acyl, alkylsulfonyl, or alkylsulfamoyl having from 1 to 6 carbon atoms; and
D is aryl or heteroaryl.

Unless stereochemistry is explicitly depicted, a structure is intended to include every possible stereoisomer, both pure or in any possible mixture. Compounds of the stereochemistry shown below, or pharmaceutically acceptable salts or prodrugs thereof, are particularly useful.

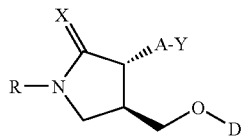

In relation to the identity of A disclosed in the chemical structures presented herein, A is —$(CH_2)_6$—, cis —$CH_2CH=CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O.

While not intending to be limiting, A may be —$(CH_2)_6$—, cis —$CH_2CH=CH$—$(CH_2)_3$—, or —$CH_2C\equiv C$—$(CH_2)_3$—.

Alternatively, A may be a group which is related to one of these three moieties in that any carbon is substituted with S and/or O. For example, while not intending to limit the scope of the invention in any way, A may be an S substituted moiety such as one of the following or the like.

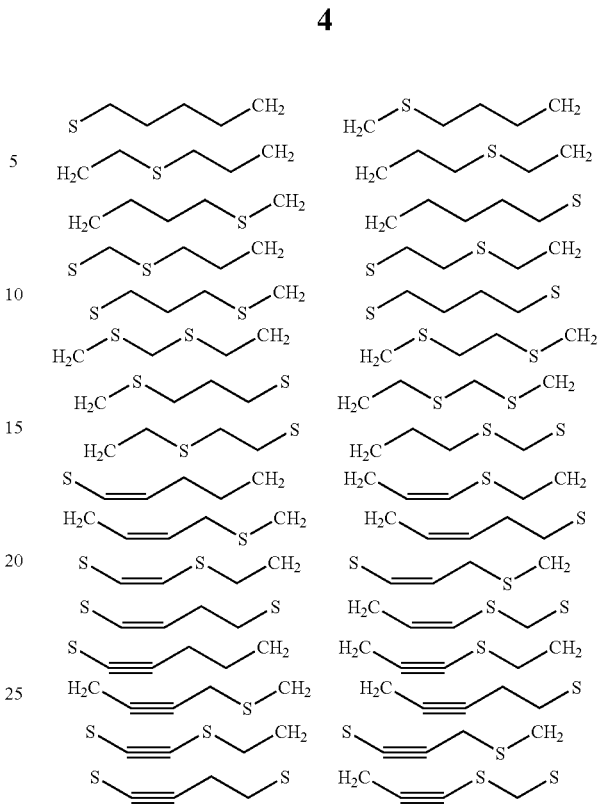

Alternatively, while not intending to limit the scope of the invention in any way, A may be an O substituted moiety such as one of the following or the like.

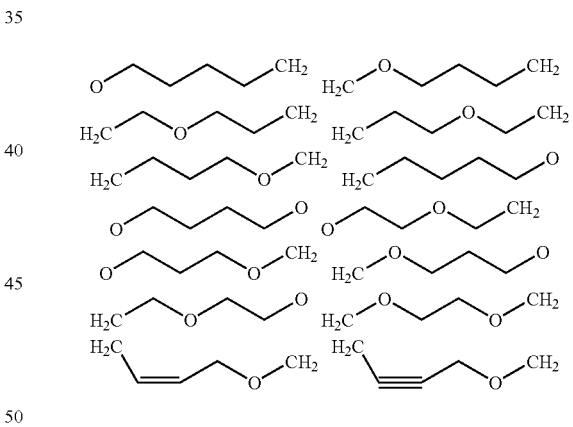

Alternatively, while not intending to limit the scope of the invention in any way, A may have both an O and an S substituted into the chain, such as one of the following or the like.

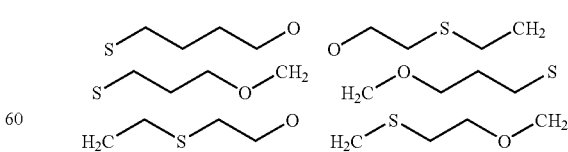

Alternatively, while not intending to limit the scope of the invention in any way, in certain embodiments A is —$(CH_2)_m$—Ar—$(CH_2)_o$— wherein Ar is interarylene or heterointerarylene, the sum of m and o is from 1 to 4, and wherein one CH₂ may be substituted with S or O. In other words, while not intending to limit the scope of the invention in any way, in one embodiment A comprises from 1 to 4 CH₂ moieties and Ar, e.g. —CH₂—Ar—, —(CH₂)₂—Ar—, —CH₂—Ar—CH₂—, —CH₂Ar—(CH₂)₂—, —(CH₂)₂—Ar—(CH₂)₂—, and the like;

in another embodiment A comprises O, from 0 to 3 CH₂ moieties, and Ar, e.g., —O—Ar—, Ar—CH₂—O—, —O—Ar—(CH₂)₂—, —O—CH₂—Ar—, —O—CH₂—Ar—(CH₂)₂, and the like; or in another embodiment A comprises S, from 0 to 3 CH₂ moieties, and Ar, e.g., —S—Ar—, Ar—CH₂—S—, —S—Ar—(CH₂)₂—, —S—CH₂—Ar—, —S—CH₂—Ar—(CH₂)₂, —(CH₂)₂—S—Ar, and the like.

In another embodiment, the sum of m and o is from 2 to 4 wherein one CH₂ may be substituted with S or O.

In another embodiment, the sum of m and o is 3 wherein one CH₂ may be substituted with S or O.

In another embodiment, the sum of m and o is 2 wherein one CH₂ may be substituted with S or O.

In another embodiment, the sum of m and o is 4 wherein one CH₂ may be substituted with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH₂)₂-Ph-. While not intending to limit scope of the invention in any way, substituents may have 4 or less heavy atoms, or in other words, non hydrogen atoms. Any number of hydrogen atoms required for a particular substituent will also be included. Thus, the substituent may be hydrocarbyl having up to 4 carbon atoms, including alkyl up to $C_4$, alkenyl, alkynyl, and the like;

hydrocarbyloxy up to $C_3$;

$CF_3$;

halo, such as F, Cl, or Br;

hydroxyl;

$NH_2$ and alkylamine functional groups up to $C_3$;

other N or S containing substituents;

and the like.

In one embodiment A is —(CH₂)$_m$—Ar—(CH₂)$_o$— wherein Ar is interphenylene, the sum of m and o is from 1 to 3, and wherein one CH₂ may be substituted with S or O.

In another embodiment A is —CH₂—Ar—OCH₂—. In another embodiment A is —CH₂—Ar—OCH₂— and Ar is interphenylene. In another embodiment, Ar is attached at the 1 and 3 positions, otherwise known as m-interphenylene, such as when A has the structure shown below.

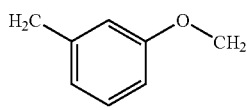

In another embodiment A is —(CH₂)₆—, cis —CH₂CH═CH—(CH₂)₃—, or —CH₂C≡C—(CH₂)₃—, wherein 1 or 2 carbon atoms may be substituted with S or O; or A is —(CH₂)₂-Ph- wherein one CH₂ may be substituted with S or O.

In another embodiment A is —(CH₂)₆—, cis —CH₂CH═CH—(CH₂)₃—, or —CH₂C≡C—(CH₂)₃—, wherein 1 or 2 carbon atoms may be substituted with S or O; or A is —(CH₂)₂-Ph-.

In other embodiments, A has one of the following structures, where Y is attached to the aromatic or heteroaromatic ring.

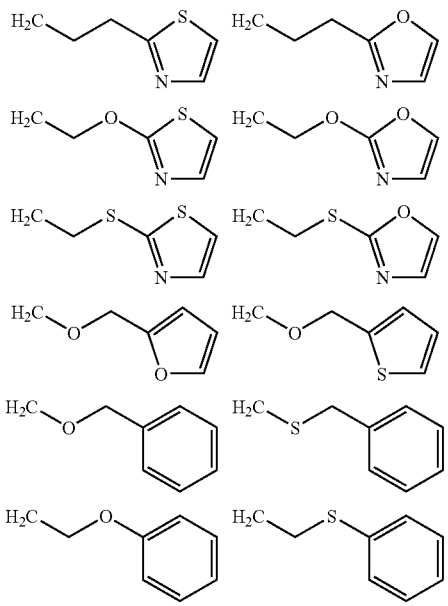

In another embodiment, A is selected from the group

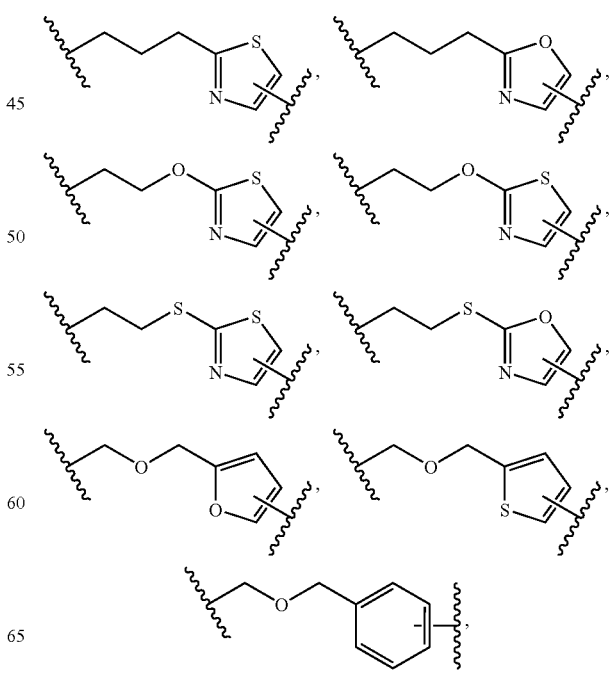

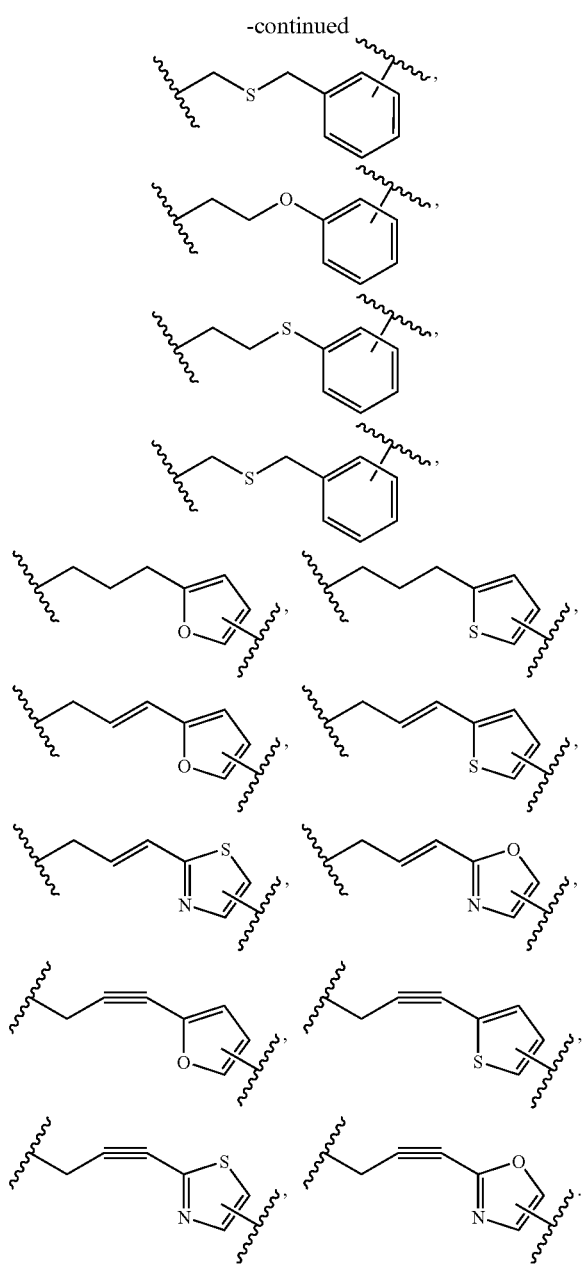

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is —(CH$_2$)$_6$—.
In another embodiment A is cis —CH$_2$CH=CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH=CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.

In another embodiment A is —CH$_2$-Ph-OCH$_2$—, wherein Ph is interphenylene.

In another embodiment A is —CH$_2$-mPh-OCH$_2$—, wherein mPh is m-interphenylene.

In another embodiment A is —CH$_2$—O—(CH$_2$)$_4$—.

In another embodiment A is —CH$_2$—O—CH$_2$—Ar—, wherein Ar is 2,5-interthienylene.

In another embodiment A is —CH$_2$—O—CH$_2$—Ar—, wherein Ar is 2,5-interfurylene.

X is S or O. Thus, compounds according to one of the formulas shown below, or pharmaceutically acceptable salts or prodrugs thereof, are possible.

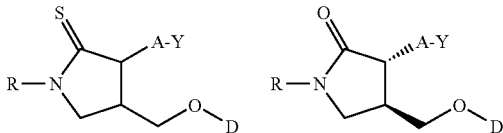

R is H; or alkyl, acyl, alkylsulfonyl, or alkylsulfamoyl having from 1 to 6 carbon atoms.

Alkyl is hydrocarbyl (i.e. all C and H atoms) having no double or triple bonds including:

linear alkyl such as methyl, ethyl, propyl, n-butyl, n-pentyl, n-hexyl, and the like;

branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;

cycloalkyl such as cyclopropyl, cyclobutyl, cyclopentyl, cyclohexyl, cycloheptyl, etc.; and alkyl fragments consisting of both cyclic and noncyclic components, whether linear or branched, which may be attached to the remainder of the molecule at any available position including terminal, internal, or ring carbon atoms.

Acyl has the meaning normally understood in the art. In other words, acyl is alkyl attached to a carbonyl carbon, i.e. alkyl-C(=O)—.

Alkylsulfonyl has the meaning normally understood in the art. In other words, alkylsulfonyl is alkyl attached to a sulfonyl sulfur, i.e. alkyl-SO$_2$—.

Alkylsulfamoyl has the meaning normally understood in the art. In other words, alkylsulfamoyl is alkyl attached to a sulfamoyl nitrogen, i.e. alkyl-N—SO$_2$—.

Thus, compounds according to one of the structures shown below, or pharmaceutically acceptable salts or prodrugs thereof, are possible, where R$^3$ is independently H or C$_{1-6}$ alkyl.

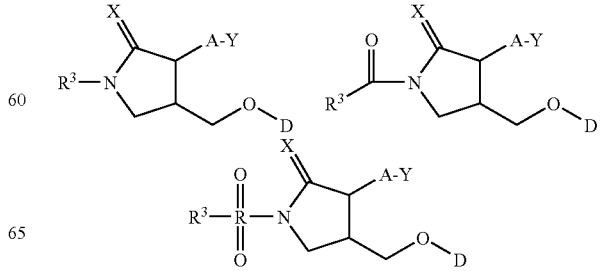

-continued

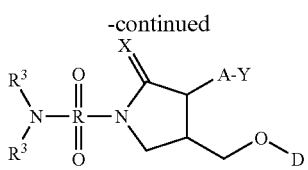

Particular embodiments contemplated include compounds according to the structures below, or pharmaceutically acceptable salts or prodrugs thereof.

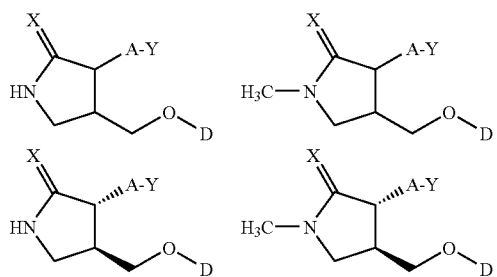

D is aryl or heteroaryl.

Aryl is an unsubstituted or substituted aromatic ring or ring system such as phenyl, naphthyl, biphenyl, and the like.

Heteroaryl is aryl having one or more N, O, or S atoms in the ring, i.e. a ring carbon is substituted by N, O, or S. While not intending to be limiting, examples of heteroaryl include unsubstituted or substituted thienyl, pyridinyl, furyl, benzothienyl, benzofuryl, imidizololyl, indolyl, and the like.

The substituents of aryl or heteroaryl may have up to 12 non-hydrogen atoms each and as many hydrogen atoms as necessary. Thus, while not intending to limit the scope of the invention in any way, the substituents may be:

hydrocarbyl, such as alkyl, alkenyl, alkynyl, and the like, including linear, branched or cyclic hydrocarbyl, and combinations thereof;

hydrocarbyloxy, meaning O-hydrocarbyl such as $OCH_3$, $OCH_2CH_3$, O-cyclohexyl, etc, up to 11 carbon atoms;

hydroxyhydrocarbyl, meaning hydrocarbyl-OH such as $CH_2OH$, $C(CH_3)_2OH$, etc, up to 11 carbon atoms;

nitrogen substituents such as $NO_2$, CN, and the like, including amino, such as $NH_2$, $NH(CH_2CH_3OH)$, $NHCH_3$, and the like up to 11 carbon atoms;

carbonyl substituents, such as $CO_2H$, ester, amide, and the like;

halogen, such as chloro, fluoro, bromo, and the like fluorocarbyl, such as $CF_3$, $CF_2CF_3$, etc.;

phosphorous substituents, such as $PO_3^{2-}$, and the like;

sulfur substituents, including S-hydrocarbyl, SH, $SO_3H$, $SO_2$-hydrocarbyl, $SO_3$-hydrocarbyl, and the like.

In certain embodiments, the number of non-hydrogen atoms is 6 or less in a substituent. In other embodiments, the number of non-hydrogen atoms is 3 or less in a substituent. In other embodiments, the number of non-hydrogen atoms on a substituent is 1.

In certain embodiments, the substituents contain only hydrogen, carbon, oxygen, halogen, nitrogen, and sulfur. In other embodiments, the substituents contain only hydrogen, carbon, oxygen, and halogen.

Unless otherwise indicated, references to aryl, heteroaryl, phenyl, thienyl, benzothienyl, and the like are intended to mean both the substituted and the unsubstituted moiety.

Thus, compounds wherein D is any of the above classes or species of aryl or heteroaryl are contemplated herein.

Further, while not intending to limit the scope of the invention in any way, in one embodiment D is phenyl. In another embodiment D is chlorophenyl, meaning phenyl with one or more chloro substituents. In another embodiment D is 3,5-dichlorophenyl. In another embodiment D is unsubstituted phenyl.

Compounds according to the structures below, or pharmaceutically acceptable salts or prodrugs thereof, are contemplated, wherein $R^4$ is independently a substituent having from 0 to 10 carbon atoms and from 0 to 5 heteroatoms selected from the group consisting of Cl, F, Br, O, N, and S; and q is 0, 1, 2, 3, or 4. $R^4$ may also form a ring with two carbon atoms of the phenyl ring.

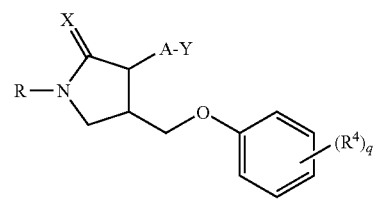

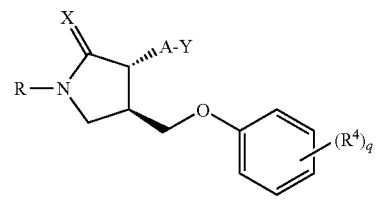

In one embodiment $R^4$ is $C_{1-6}$ alkyl, $C_{1-6}$ hydroxyalkyl, $C_{1-6}$ O-alkyl, $C_{1-6}$ aryl, $C_{1-6}$ alkylsulfamoyl, $C_{1-10}$ aryl, $C_{1-10}$ arylalkyl, $C_{1-10}$ hydroxyarylalkyl, Cl, F, Br, $CF_3$, $COCF_3$, $SO_2NH_2$, $NO_2$, OH, or CN.

Arylalkyl is alkyl with an aryl substituent.

Hydroxyarylalkyl is alkyl with an aryl and a hydroxyl substituent.

Each of the compounds or structures shown below represents an individual embodiment contemplated herein. Pharmaceutically acceptable salts or prodrugs of these compounds or structures are also contemplated.

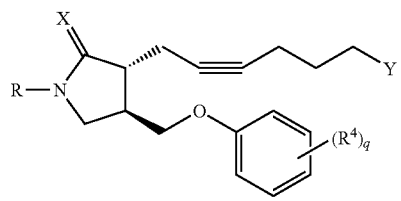

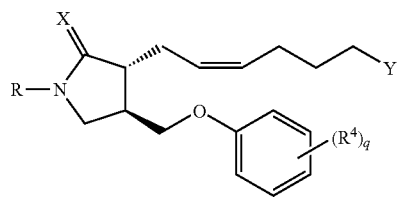

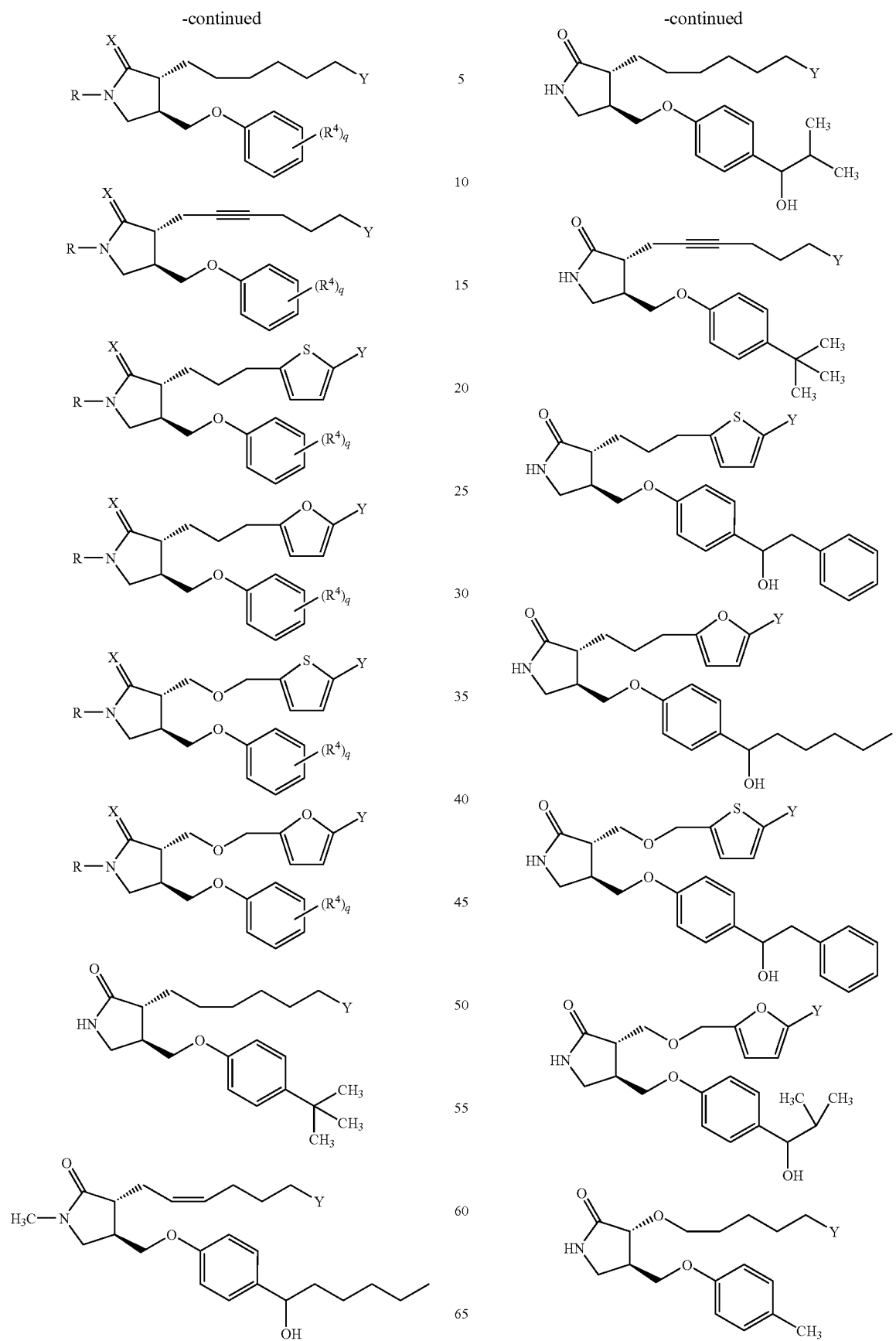

-continued
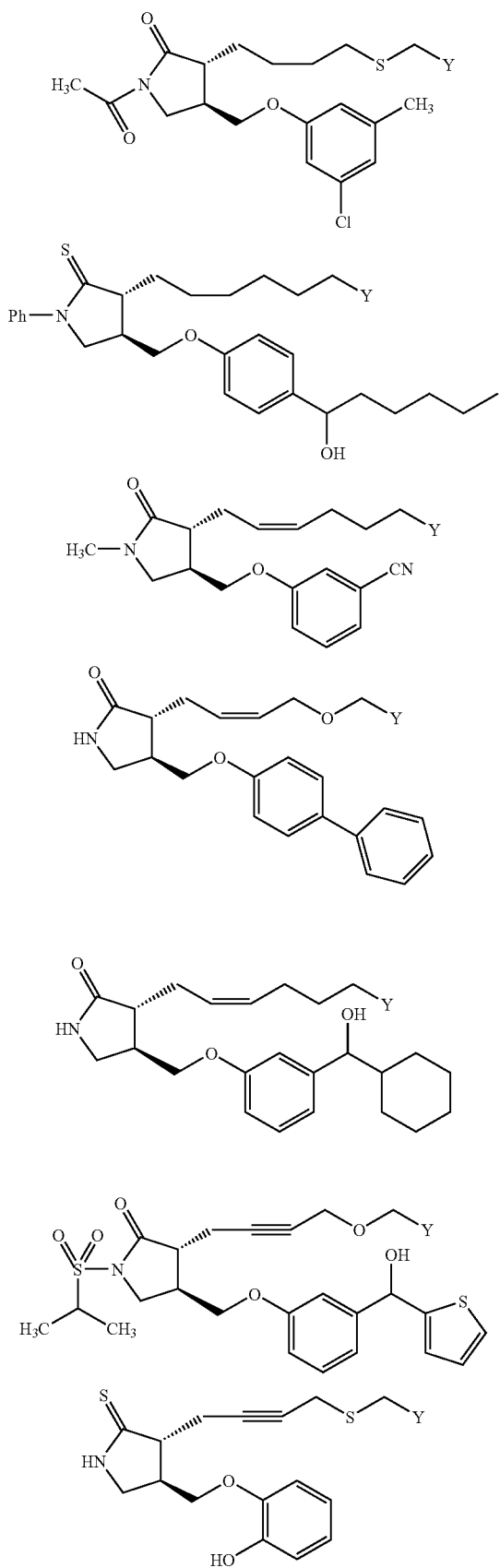
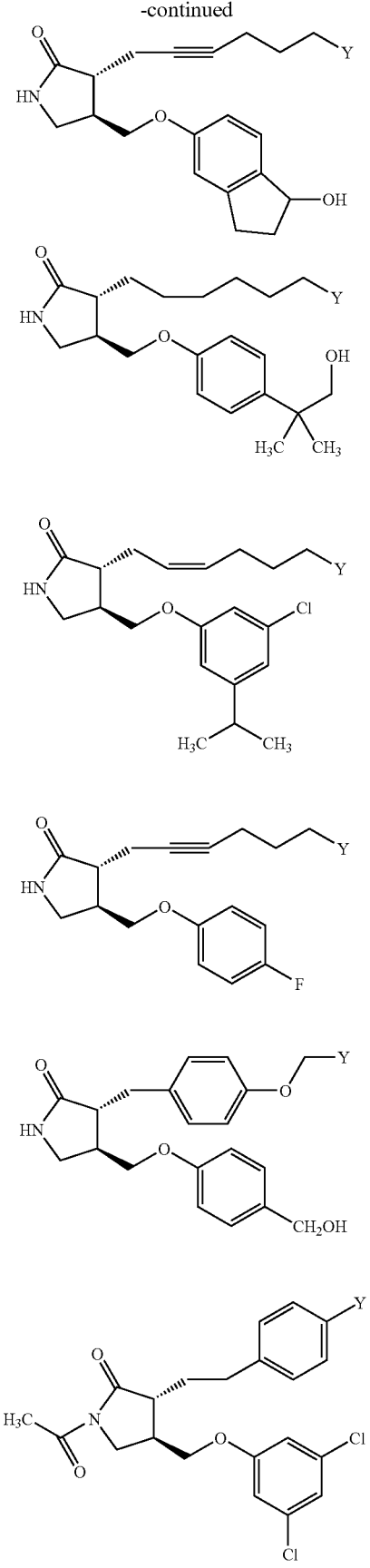

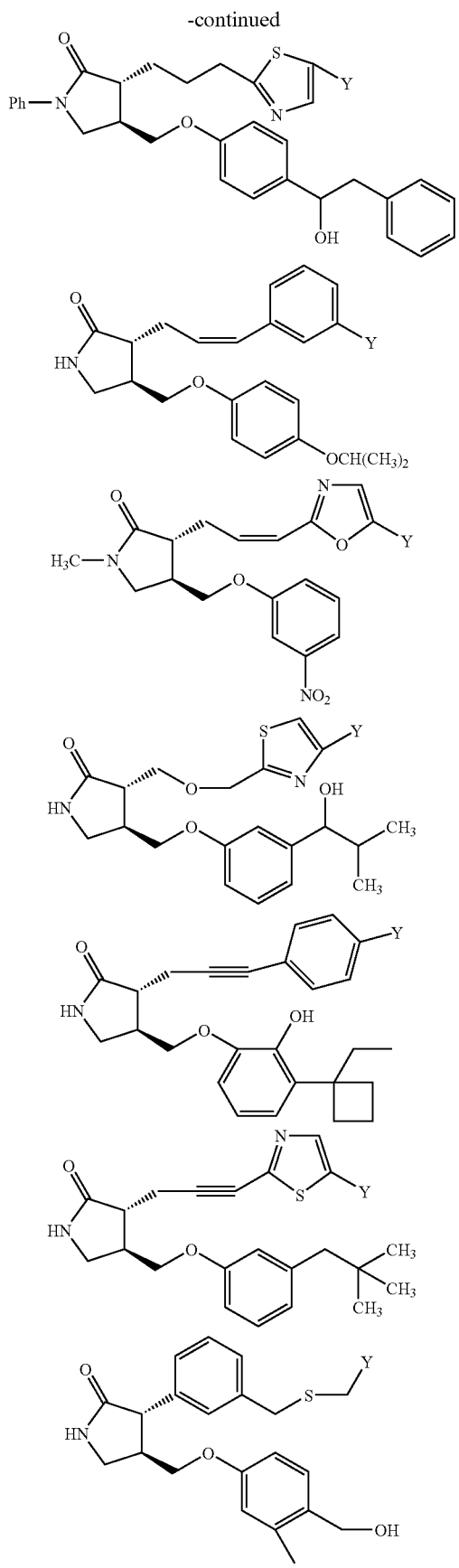

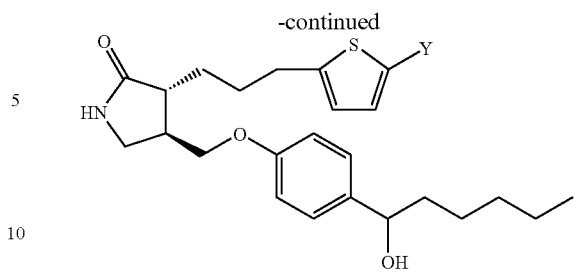

Specifically Contemplated Embodiments

Embodiments are contemplated for each of the compounds or structural descriptions of compounds disclosed herein. Furthermore, for each compound or structure a method of treating glaucoma or ocular hypertension, a method of treating inflammatory bowel disease, a method of manufacturing a medicament for the treatment of glaucoma or ocular hypertension, a method of manufacturing a medicament for the treatment of inflammatory bowel disease, and a composition comprising a therapeutically effective amount of the compound is specifically contemplated. Furthermore, the embodiments disclosed below are specifically contemplated.

Methods of Manufacturing A Medicament

Glaucoma or Ocular Hypertension

One embodiment is use of a compound in the manufacture of a medicament for the treatment of glaucoma or ocular hypertension, said compound comprising

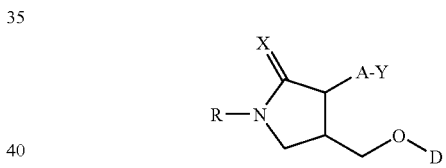

or a pharmaceutically acceptable salt or a prodrug thereof;

wherein
Y is

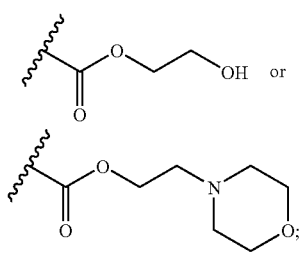

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

X is S or O;

R is H; or alkyl, acyl, alkylsulfonyl, or alkylsulfamoyl having from 1 to 6 carbon atoms; and D is aryl or heteroaryl.

In another embodiment said compound comprises

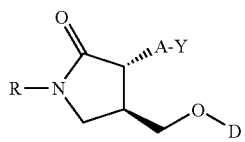

or a pharmaceutically acceptable salt or a prodrug thereof.
In another embodiment said compound comprises

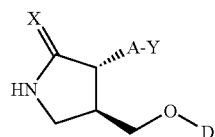

or a pharmaceutically acceptable salt or a prodrug thereof.
In another embodiment said compound comprises

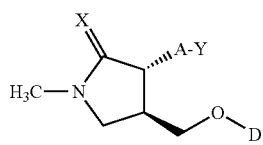

or a pharmaceutically acceptable salt or a prodrug thereof.
In another embodiment said compound comprises

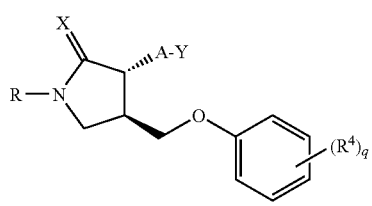

or a pharmaceutically acceptable salt or a prodrug thereof
wherein $R^4$ is independently a substituent having from 0 to 10 carbon atoms and from 0 to 5 heteroatoms selected from the group consisting of Cl, F, Br, O, N, and S;
q is 0, 1, 2, 3, or 4; and
wherein two $R^4$ moieties may form a ring with two carbon atoms of the phenyl ring.
In another embodiment said compound comprises

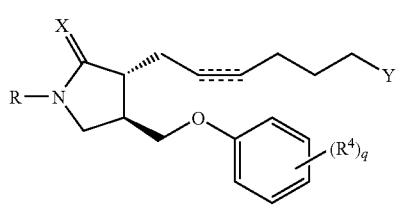

or a pharmaceutically acceptable salt or a prodrug thereof.

In another embodiment said compound comprises

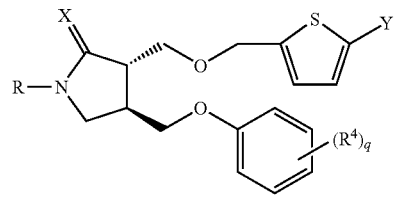

or a pharmaceutically acceptable salt or a prodrug thereof.
In another embodiment said compound comprises

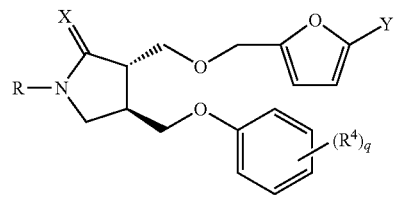

or a pharmaceutically acceptable salt or a prodrug thereof.

Inflammatory Bowel Disease

One embodiment is use of a compound in the manufacture of a medicament for the treatment of inflammatory bowel disease. said compound comprising

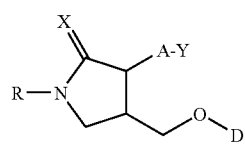

or a pharmaceutically acceptable salt or a prodrug thereof;
wherein
Y is

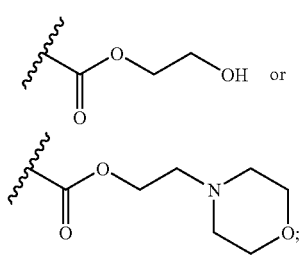

A is —$(CH_2)_6$—, cis —$CH_2CH{=}CH$—$(CH_2)_3$—, or —$CH_2C{\equiv}C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;
X is S or O;
R is H; or alkyl, acyl, alkylsulfonyl, or alkylsulfamoyl having from 1 to 6 carbon atoms; and
D is aryl or heteroaryl.

In another embodiment said compound comprises

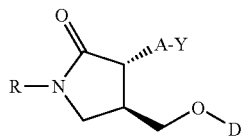

or a pharmaceutically acceptable salt or a prodrug thereof.
In another embodiment said compound comprises

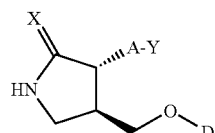

or a pharmaceutically acceptable salt or a prodrug thereof.
In another embodiment said compound comprises

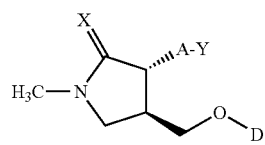

or a pharmaceutically acceptable salt or a prodrug thereof.
In another embodiment said compound comprises

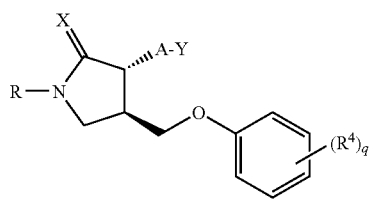

or a pharmaceutically acceptable salt or a prodrug thereof
wherein $R^4$ is independently a substituent having from 0 to 10 carbon atoms and from 0 to 5 heteroatoms selected from the group consisting of Cl, F, Br, O, N, and S;
q is 0, 1, 2, 3, or 4; and
wherein two $R^4$ moieties may form a ring with two carbon atoms of the phenyl ring.
In another embodiment said compound comprises

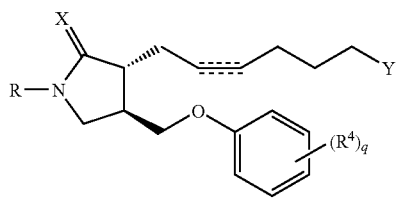

or a pharmaceutically acceptable salt or a prodrug thereof.

In another embodiment said compound comprises

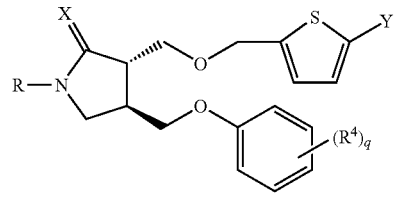

or a pharmaceutically acceptable salt or a prodrug thereof.
In another embodiment said compound comprises

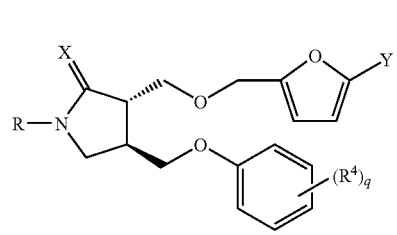

or a pharmaceutically acceptable salt or a prodrug thereof.
In another embodiment the inflammatory bowel disease is ulcerative colitis.
In another embodiment the inflammatory bowel disease is Crohn's disease.

Baldness

One embodiment is use of a compound in the manufacture of a medicament for the treatment of baldness.
said compound comprising

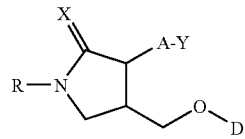

or a pharmaceutically acceptable salt or a prodrug thereof;
wherein
Y is

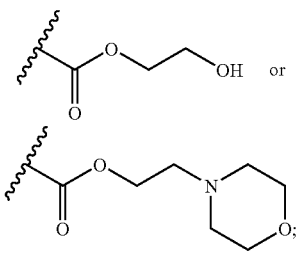

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

X is S or O;

R is H; or alkyl, acyl, alkylsulfonyl, or alkylsulfamoyl having from 1 to 6 carbon atoms; and D is aryl or heteroaryl.

In another embodiment said compound comprises

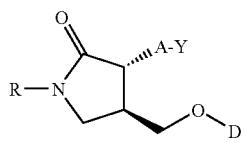

or a pharmaceutically acceptable salt or a prodrug thereof.

In another embodiment said compound comprises

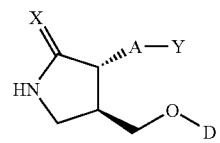

or a pharmaceutically acceptable salt or a prodrug thereof.

In another embodiment said compound comprises

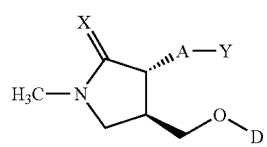

or a pharmaceutically acceptable salt or a prodrug thereof.

In another embodiment said compound comprises

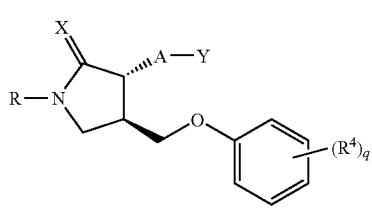

or a pharmaceutically acceptable salt or a prodrug thereof wherein R$^4$ is independently a substituent having from 0 to 10 carbon atoms and from 0 to 5 heteroatoms selected from the group consisting of Cl, F, Br, O, N, and S;

q is 0, 1, 2, 3, or 4; and wherein two R$^4$ moieties may form a ring with two carbon atoms of the phenyl ring.

In another embodiment said compound comprises

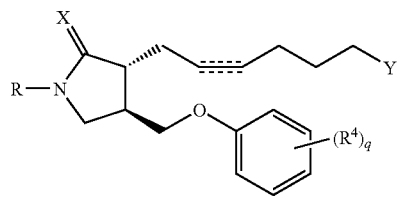

or a pharmaceutically acceptable salt or a prodrug thereof.

In another embodiment said compound comprises

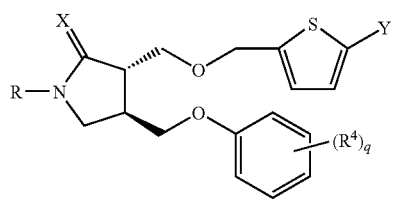

or a pharmaceutically acceptable salt or a prodrug thereof.

In another embodiment said compound comprises

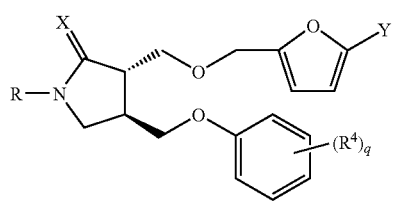

or a pharmaceutically acceptable salt or a prodrug thereof.

Methods of Treating

Glaucoma or Ocular Hypertension

One embodiment is a method comprising administering a compound to a mammal for the treatment of glaucoma or ocular hypertension, said compound comprising

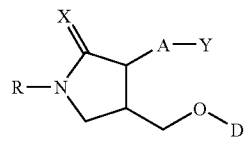

or a pharmaceutically acceptable salt or a prodrug thereof;

wherein

Y is

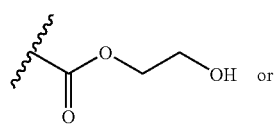

or

-continued

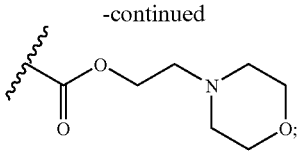

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

X is S or O;

R is H; or alkyl, acyl, alkylsulfonyl, or alkylsulfamoyl having from 1 to 6 carbon atoms; and D is aryl or heteroaryl.

In another embodiment said compound comprises

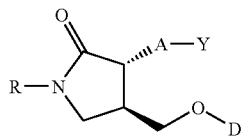

or a pharmaceutically acceptable salt or a prodrug thereof.

In another embodiment said compound comprises

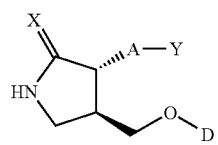

or a pharmaceutically acceptable salt or a prodrug thereof.

In another embodiment said compound comprises

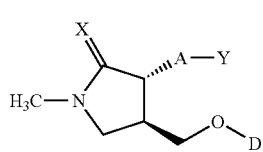

or a pharmaceutically acceptable salt or a prodrug thereof.

In another embodiment said compound comprises

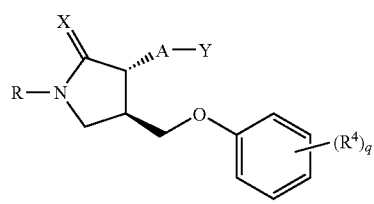

or a pharmaceutically acceptable salt or a prodrug thereof wherein R$^4$ is independently a substituent having from 0 to 10 carbon atoms and from 0 to 5 heteroatoms selected from the group consisting of Cl, F, Br, O, N, and S;

q is 0, 1, 2, 3, or 4; and wherein two R$^4$ moieties may form a ring with two carbon atoms of the phenyl ring.

In another embodiment said compound comprises

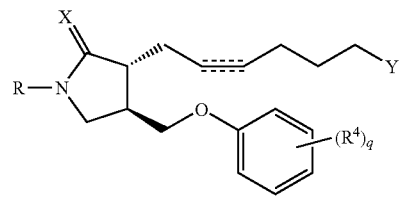

or a pharmaceutically acceptable salt or a prodrug thereof.

In another embodiment said compound comprises

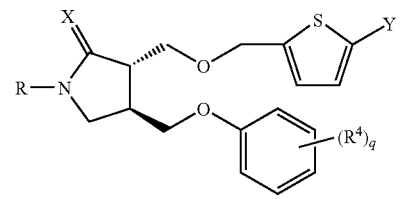

or a pharmaceutically acceptable salt or a prodrug thereof.

In another embodiment said compound comprises

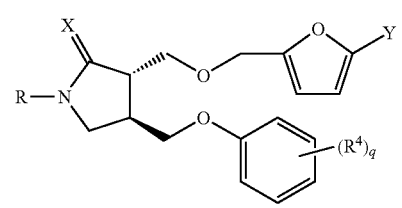

or a pharmaceutically acceptable salt or a prodrug thereof.

Inflammatory Bowel Disease

One embodiment is a method comprising administering a compound to a mammal for the treatment of inflammatory bowel disease.

said compound comprising

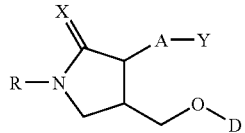

or a pharmaceutically acceptable salt or a prodrug thereof;

wherein
Y is

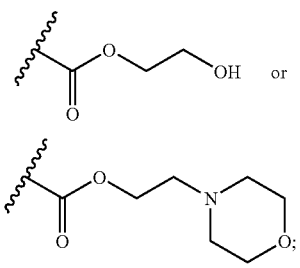

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

X is S or O;

R is H; or alkyl, acyl, alkylsulfonyl, or alkylsulfamoyl having from 1 to 6 carbon atoms; and D is aryl or heteroaryl.

In another embodiment said compound comprises

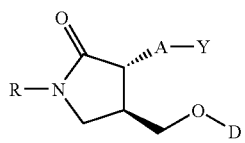

or a pharmaceutically acceptable salt or a prodrug thereof.
In another embodiment said compound comprises

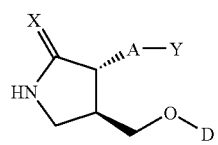

or a pharmaceutically acceptable salt or a prodrug thereof.
In another embodiment said compound comprises

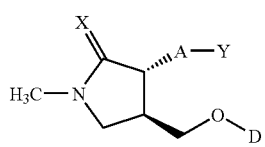

or a pharmaceutically acceptable salt or a prodrug thereof.

In another embodiment said compound comprises

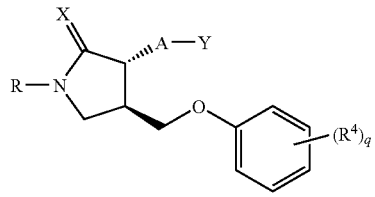

or a pharmaceutically acceptable salt or a prodrug thereof
wherein R$^4$ is independently a substituent having from 0 to 10 carbon atoms and from 0 to 5 heteroatoms selected from the group consisting of Cl, F, Br, O, N, and S;

q is 0, 1, 2, 3, or 4; and wherein two R$^4$ moieties may form a ring with two carbon atoms of the phenyl ring.

In another embodiment said compound comprises

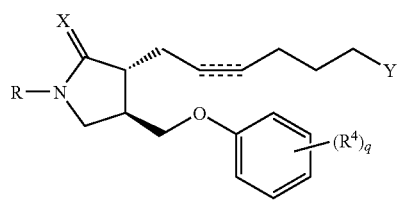

or a pharmaceutically acceptable salt or a prodrug thereof.
In another embodiment said compound comprises

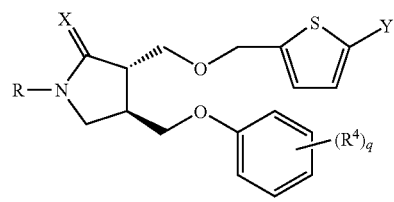

or a pharmaceutically acceptable salt or a prodrug thereof.
In another embodiment said compound comprises

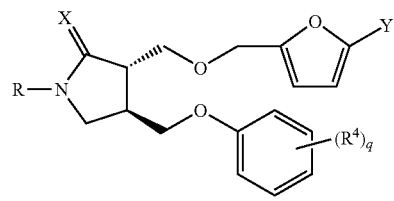

or a pharmaceutically acceptable salt or a prodrug thereof.
In another embodiment the inflammatory bowel disease is ulcerative colitis.

In another embodiment the inflammatory bowel disease is Crohn's disease.

Compounds
One embodiment is a compound comprising

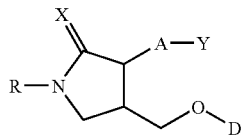

or a pharmaceutically acceptable salt or a prodrug thereof;
wherein
Y is

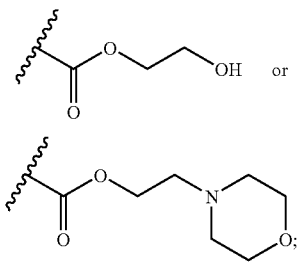

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

X is S or O;

R is H; or alkyl, acyl, alkylsulfonyl, or alkylsulfamoyl having from 1 to 6 carbon atoms; and D is aryl or heteroaryl.

Another embodiment is a compound comprising

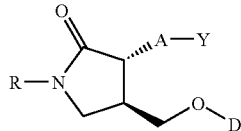

or a pharmaceutically acceptable salt or a prodrug thereof.
Another embodiment is a compound comprising

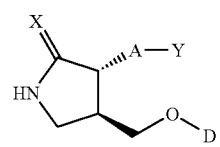

or a pharmaceutically acceptable salt or a prodrug thereof.

Another embodiment is a compound comprising

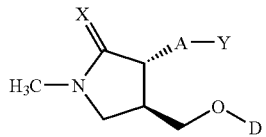

or a pharmaceutically acceptable salt or a prodrug thereof.
Another embodiment is a compound comprising

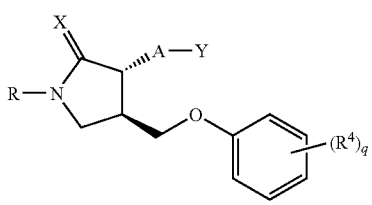

or a pharmaceutically acceptable salt or a prodrug thereof
wherein R$^4$ is independently a substituent having from 0 to 10 carbon atoms and from 0 to 5 heteroatoms selected from the group consisting of Cl, F, Br, O, N, and S;

q is 0, 1, 2, 3, or 4; and wherein two R$^4$ moieties may form a ring with two carbon atoms of the phenyl ring.

Another embodiment is a compound comprising

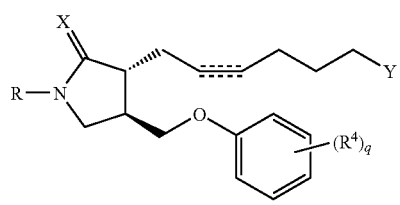

or a pharmaceutically acceptable salt or a prodrug thereof.
Another embodiment is a compound comprising

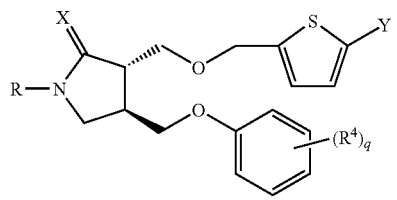

or a pharmaceutically acceptable salt or a prodrug thereof.

Another embodiment is a compound comprising

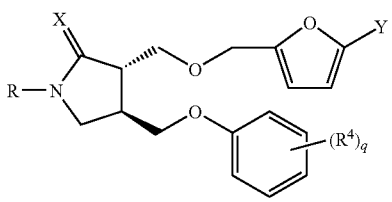

or a pharmaceutically acceptable salt or a prodrug thereof.

Composition

Another embodiment is a composition wherein said composition comprises a compound

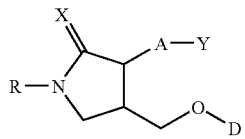

or a pharmaceutically acceptable salt or a prodrug thereof;

wherein

Y is

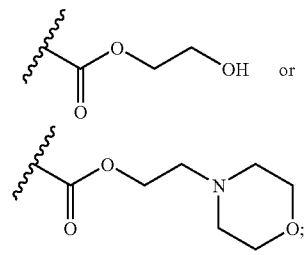

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

X is S or O;

R is H; or alkyl, acyl, alkylsulfonyl, or alkylsulfamoyl having from 1 to 6 carbon atoms; and D is aryl or heteroaryl.

In another embodiment said compound comprises

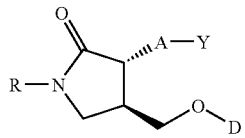

or a pharmaceutically acceptable salt or a prodrug thereof.

In another embodiment said compound comprises

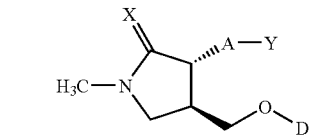

or a pharmaceutically acceptable salt or a prodrug thereof.

In another embodiment said compound comprises

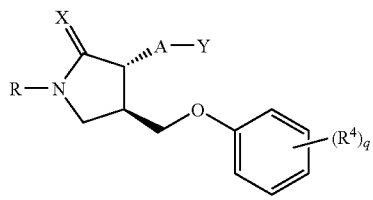

or a pharmaceutically acceptable salt or a prodrug thereof.

In another embodiment said compound comprises

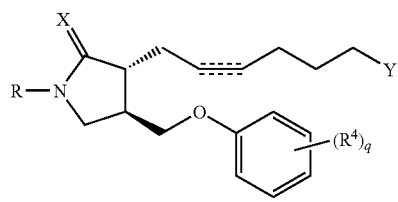

or a pharmaceutically acceptable salt or a prodrug thereof wherein R$^4$ is independently a substituent having from 0 to 10 carbon atoms and from 0 to 5 heteroatoms selected from the group consisting of Cl, F, Br, O, N, and S;

q is 0, 1, 2, 3, or 4; and wherein two R$^4$ moieties may form a ring with two carbon atoms of the phenyl ring.

In another embodiment said compound comprises

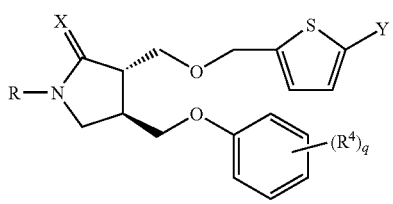

or a pharmaceutically acceptable salt or a prodrug thereof.

In another embodiment said compound comprises or a pharmaceutically acceptable salt or a prodrug thereof.

In another embodiment said compound comprises

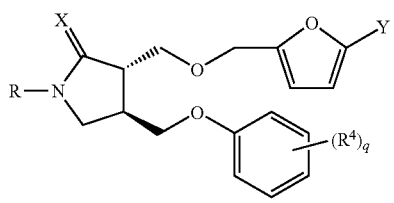

or a pharmaceutically acceptable salt or a prodrug thereof.

In another embodiment the inflammatory bowel disease is ulcerative colitis.

In another embodiment the inflammatory bowel disease is Crohn's disease.

Methods of Treating

One embodiment is a composition comprising a compound, wherein said composition is ophthalmically acceptable, said compound comprising

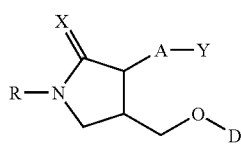

or a pharmaceutically acceptable salt or a prodrug thereof;

wherein

Y is

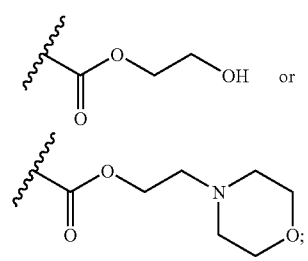

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

X is S or O;

R is H; or alkyl, acyl, alkylsulfonyl, or alkylsulfamoyl having from 1 to 6 carbon atoms; and D is aryl or heteroaryl.

In another embodiment said compound comprises

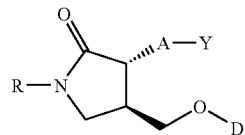

or a pharmaceutically acceptable salt or a prodrug thereof.
In another embodiment said compound comprises

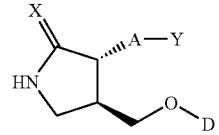

or a pharmaceutically acceptable salt or a prodrug thereof.
In another embodiment said compound comprises

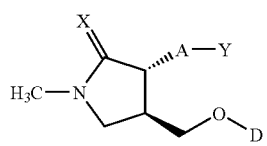

or a pharmaceutically acceptable salt or a prodrug thereof.
In another embodiment said compound comprises

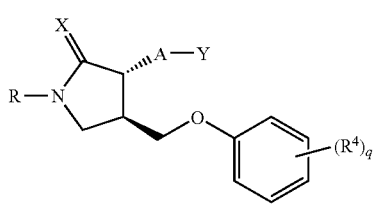

or a pharmaceutically acceptable salt or a prodrug thereof
wherein R$^4$ is independently a substituent having from 0 to 10 carbon atoms and from 0 to 5 heteroatoms selected from the group consisting of Cl, F, Br, O, N, and S;

q is 0, 1, 2, 3, or 4; and wherein two R$^4$ moieties may form a ring with two carbon atoms of the phenyl ring.

In another embodiment said compound comprises

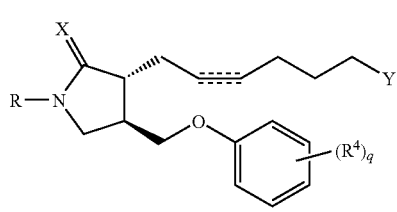

or a pharmaceutically acceptable salt or a prodrug thereof.

In another embodiment said compound comprises

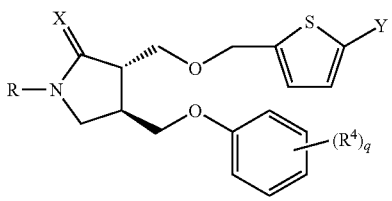

or a pharmaceutically acceptable salt or a prodrug thereof.

In another embodiment said compound comprises

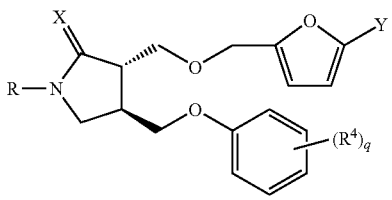

or a pharmaceutically acceptable salt or a prodrug thereof.

The compounds of disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physiologicla acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chlorprostenol, fluprostenol, 13,14-dihydro-chlorprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

These compounds can also be used to treat or prevent conditions affecting the posterior part of the eye include maculopathies/retinal degeneration such as non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis. Preferably, the disease or condition is retinitis pigmentosa, proliferative vitreal retinopathy (PVR), age-related macular degeneration (ARMD), diabetic retinopathy, diabetic macular edema, retinal detachment, retinal tear, uveitus, or cytomegalovirus retinitis.

These compounds are also useful in treating asthma.

EXAMPLES

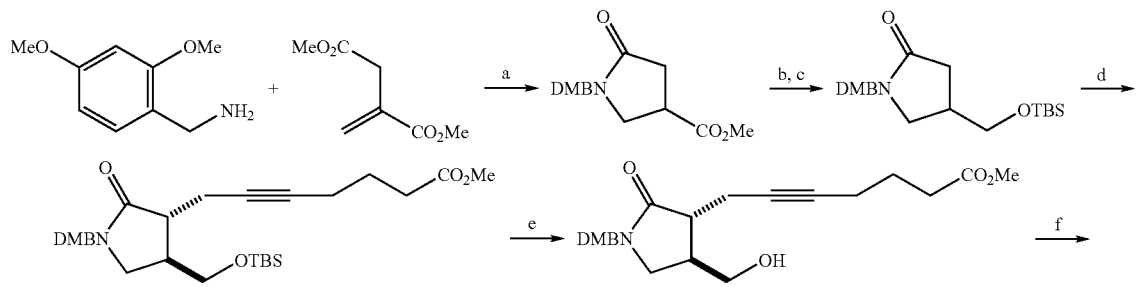

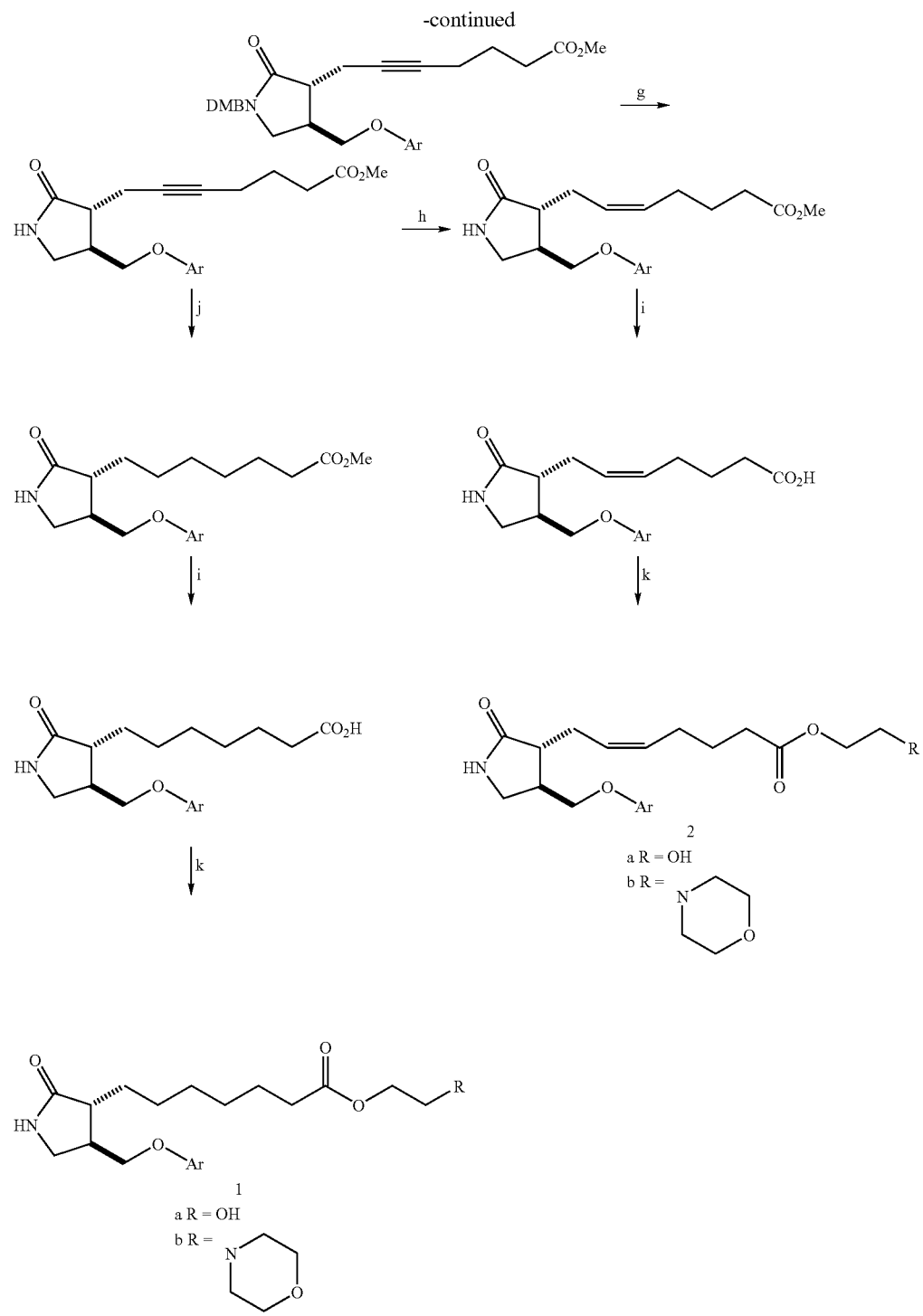
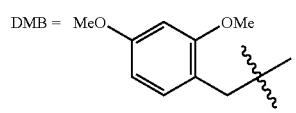
(a) MeOH, rt; (b) NaBH₄, EtOH; (c) TBSCl, imidazole, DMF; (d) i) LDA, THF; ii) HMPA, methyl 7-iodohept-5-ynoate, THF;
(e) TBAF, THF; (f) ArOH, DIAD, PPh₃, CH₂Cl₂; (g) DDQ, CHCl₃, H₂O; (h) NiCl₂, NaBH₄, ethylene diamine, H₂, EtOH;
(i) Rabbit liver esterase, pH 7.2 buffer, MeCN; (j) Pd/C, EtOAc; (k) 1. ClCO₂Et, Et₃N, CH₂Cl₂, 2. RCH₂CH₂OH.

Step a. 1-(2,4-Dimethoxybenzyl)-5-oxo-pyrrolidine-3-carboxylic Acid Methyl Ester A solution of dimethyl itaconate (4.08 g, 25.8 mmol) in MeOH (3.2 mL) was added to a solution of 2,4-dimethoxybenzylamine (4.32 g, 25.8 mmol) in MeOH (9.6 mL) via cannula at room temperature. After 18 h at room temperature the reaction was concentrated in vacuo to afford crude 1-(2,4-dimethoxybenzyl)-5-oxo-pyrrolidine-3-carboxylic acid methyl ester as a viscous oil.

Step b. 1-(2,4-Dimethoxybenzyl)-4-hydroxymethyl-pyrrolidin-2-one

Sodium borohydride (9.76 g, 25.8 mmol) was added in three portions to a solution of the crude ester from step 1 (~25.8 mmol) in ethanol (111 mL) at 0° C. The reaction was allowed to warm to room temperature. After 18 h at room temperature, the reaction was quenched with saturated aqueous $NH_4Cl$ (100 mL) and the ethanol was removed in vacuo. The remaining aqueous mixture was extracted with EtOAc (3×100 mL). Combined extracts were dried ($Na_2SO_4$), filtered and concentrated in vacuo to afford crude 1-(2,4-dimethoxybenzyl)-4-hydroxymethyl-pyrrolidin-2-one.

Step c. 4-(tert-Butyldimethylsilanyloxymethyl)-1-(2,4-dimethoxybenzyl)-pyrrolidin-2-one Imidazole (4.39 g, 64.5 mmol) and tert-butyldimethylsilyl chloride (4.28 g, 28.4 mmol) were added to a solution of the crude alcohol from step 2 (~25.8 mmol) in DMF (36 mL). After 18 h at room temperature, the reaction was diluted with hexane (400 mL) and washed with water (2×200 mL) and brine (200 mL). The organic phase was dried ($MgSO_4$), filtered and concentrated to afford 9.47 g (97%) of 4-(tert-butyldimethylsilanyloxymethyl)-1-(2,4-dimethoxybenzyl)-pyrrolidin-2-one as a colorless oil.

Step d. 7-[(3R*,4R*)-4-(tert-Butyldimethylsilanyloxymethyl)-1-(2,4-dimethoxybenzyl)-2-oxo-pyrrolidin-3-yl]-hept-5-ynoic Acid Methyl Ester Lithium diisopropylamide (1.5 M in cyclohexane, 9.22 mL, 13.83 mmol) was added to a solution of 4-(tert-butyldimethylsilanyloxymethyl)-1-(2,4-dimethoxybenzyl)-pyrrolidin-2-one (2.63 g, 6.93 mmol) in THF (41 mL) at −78° C. under nitrogen. After 30 min at −78° C., hexamethylphosphoramide (3.61 mL, 20.7 mmol) was added dropwise. After 30 min at −78° C., methyl 7-iodohept-5-ynoate (5.52 g, 20.7 mmol) in THF (20 mL +3 mL) was added. The reaction mixture was allowed to warm to room temperature. After 18 h at room temperature, the reaction was quenched with saturated aqueous $NH_4Cl$ and extracted with EtOAc (3×50 mL). Combined extracts were dried ($Na_2SO_4$), filtered and concentrated in vacuo. The crude residue was purified by flash column chromatography on silica gel (40% EtOAc/hexane) to afford 579 mg (16%) of 7-[(3R*,4R*)-4-(tert-butyldimethylsilanyloxymethyl)-1-(2,4-dimethoxybenzyl)-2-oxo-pyrrolidin-3-yl]-hept-5-ynoic acid methyl ester.

Step e. 7-[(3R*,4R*)-1-(2,4-Dimethoxybenzyl)-4-hydroxymethyl-2-oxo-pyrrolidin-3-yl]-hept-5-ynoic Acid Methyl Ester Tetrabutylammonium fluoride (1.0 M in THF, 4.0 mL, 4.0 mmol) was added to a solution of 7-[(3R*,4R*)-4-(tert-butyldimethylsilanyloxymethyl)-1-(2,4-dimethoxybenzyl)-2-oxo-pyrrolidin-3-yl]-hept-5-ynoic acid methyl ester (680 mg, 1.31 mmol) in THF (13 mL) at 0° C. under nitrogen. The reaction was allowed to warm to room temperature. After 18 h at room temperature, THF was removed in vacuo and the residue was taken up in EtOAc (50 mL). The organic phase was washed with water (2×20 mL) and brine (20 mL) then dried ($Na_2SO_4$), filtered and concentrated in vacuo. The crude residue was purified by flash column chromatography on silica gel (85% EtOAc/hexane→EtOAc, gradient) to afford 304 mg (57%) of 7-[(3R*,4R*)-1-(2,4-dimethoxybenzyl)-4-hydroxymethyl-2-oxo-pyrrolidin-3-yl]-hept-5-ynoic Acid Methyl Ester.

Step f.

This step is carried out with a procedure analogous to that disclosed in United States Provisional Application Ser. No. 60/644,069, filed Jan. 14, 2005 (now PCT/US 2006/000831 filed Jan. 10, 2006) (FIG. 1, Example 1, step 1).

Step g.

(DDQ, 90 mg, 0.40 mmol) is added to the compound (~0.27 mmol) in $CHCl_3$ (~1.3 mL) and water (70 μL) at room temperature. After 42 h at room temperature, the mixture is filtered through celite, washing with $CHCl_3$, concentrated in vacuo, and purified by flash column chromatography on silica gel (75% EtOAc/hexane→EtOAc→5% MeOH/EtOAc, gradient).

Step h.

Sodium borohydride (5.4 mg, 0.14 mmol) is added to a suspension of nickel (II) chloride (37 mg, 0.29 mmol) and 95% ethanol (2.3 mL). The mixture immediately turns black. More sodium borohydride (~1 mg) is added to generate a fine black suspension. After 15 min at room temperature, ethylene diamine (31 μL, 0.46 mmol) is added. After another 15 min at room temperature, the alkyne (~0.057 mmol) in 95% ethanol (0.3 mL) is added via cannula. A hydrogen atmosphere is established by evacuating and refilling with hydrogen (3x) and the reaction mixture is stirred under a balloon of hydrogen for 18 h. The reaction mixture is filtered through celite, washing with ethanol, and the filtrate is concentrated in vacuo. Purification of the resulting residue by flash column chromatography (8% MeOH/$CH_2Cl_2$) affords the desired alkene.

Step j.

Palladium on carbon (5 wt %, 10 mg) is added to a solution of the alkyne (~0.028 mmol) in EtOAc (~0.6 mL). A hydrogen atmosphere is established by evacuating and refilling with hydrogen (3x) and the reaction mixture is stirred under a balloon of hydrogen for 18 h. The reaction mixture is filtered through celite, washing with EtOAc, and the filtrate is concentrated in vacuo. Purification of the resulting residue by flash column chromatography ($CH_2Cl_2$→8% MeOH/$CH_2Cl_2$) affords the desired alkane.

Step i.

Ester hydrolysis. Rabbit liver esterase (134 units/mg, 1 mg) is added to the methyl ester (~0.012 mmol) in acetonitrile (~0.1 mL) and pH 7.2 phosphate buffer (~0.58 mL). After 18 h, methanol (5 mL) is added and the reaction mixture is concentrated to dryness in vacuo. Purification of the residue by flash column chromatography on silica gel ($CH_2Cl_2$→10% MeOH/$CH_2Cl_2$, gradient) affords the desired carboxylic acid.

Step j.

a. Triethylamine and ethyl chloroformate are added sequentially to a solution of the compound formed in step h or j in $CH_2Cl_2$ at room temperature. After 2.5 h, triethylamine and ethylene glycol are added. After stirring overnight at room temperature, the reaction mixture is partitioned between $H_2O$ and $CH_2Cl_2$. The phases are separated and the aqueous phase is extracted with $CH_2Cl_2$ (2x). The combined organic phase is washed with 1 N HCl then dried ($MgSO_4$), filtered and concentrated in vacuo. Purification of the residue by flash column chromatography on silica gel (10% $CH_3OH$/$CH_2Cl_2$) affords the desired compound.

b. Triethylamine and ethyl chloroformate are added sequentially to a solution of the compound formed in step h or j in $CH_2Cl_2$ at room temperature. After 2.5 h, triethylamine and 4-(2-hydroxyethyl)-morphine are added. After stirring overnight at room temperature, the reaction mixture is partitioned between $H_2O$ and $CH_2Cl_2$. The phases are separated and the aqueous phase is extracted with $CH_2Cl_2$ (2x). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords the desired compound the desired compound.

The enantiomers may be resolved at several stages. For instance, the intermediate alcohol (after step e or a similar alcohol lacking the alpha chain) may be resolved by enzymatic acylation or deacylation of a corresponding ester derivative. Several precedents exist in the art.

Other methods well known in the art may be used to accomplish the synthesis outlined above.

Different alpha chains may be added by a variety of methods known in the art. For example, the 7-iodohept-5-ynoate of step d may be substituted with compound 12-3 (FIG. 13) of U.S. patent application Ser. No. 11/009,298, filed on Dec. 10, 2004, now U.S. Pat. No. 7,091,231, issued Aug. 15, 2006. The 7-iodohept-5-ynoate of step d may also be substituted with a compound such as that described by Kotake (J. Med. Chem. 1994, 37, 1616-1624). Other methods are also envisioned, such as addition of methyl 5-(3-bromopropyl)thiophene-2-carboxylate (synthesis described in WO94/13295).

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid to the colons of humans in clinical trials for the treatment of inflammatory bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, commercially provides pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

Compounds 1a, 1b, 2a and 2b from above are tested in vivo to measure its ability to reduce intraocular pressure. Compound 1a is tested in normotensive dogs. The intraocular pressure (IOP) decreases from baseline. This compound is also tested in laser-induced hypertensive monkeys, the IOP decreases from baseline.

Compound 1b is tested in normotensive dogs. The intraocular pressure (IOP) decreases from baseline. This compound is also tested in laser-induced hypertensive monkeys, the IOP decreases from baseline.

Compound 2a is tested in normotensive dogs. The intraocular pressure (IOP) decreases from baseline. This compound is also tested in laser-induced hypertensive monkeys, the IOP decreases from baseline.

Compound 2b is tested in normotensive dogs. The intraocular pressure (IOP) decreases from baseline. This compound is also tested in laser-induced hypertensive monkeys, the IOP decreases from baseline.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of the formula

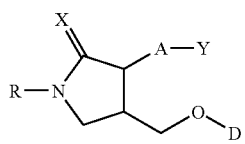

or a pharmaceutically acceptable salt thereof;

Y is

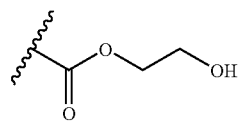 or 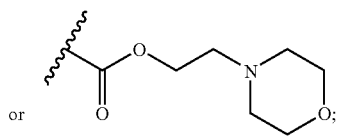;

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O;

X is S or O;

R is H; or alkyl, acyl, alkylsulfonyl, or alkylsulfamoyl having from 1 to 6 carbon atoms; and D is aryl or heteroaryl.

2. The compound of claim 1 wherein A is 5-(3-propyl)thiophen-2-yl.

3. The compound of claim 1 wherein A is 6-hexyl.

4. The compound of claim 1 wherein A is (Z)-6-hex-4-enyl.

5. The compound of claim 1 wherein B is substituted phenyl.

6. The compound of claim 1 of the formula

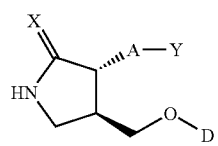

or a pharmaceutically acceptable salt thereof.

7. The compound of claim 1 of the formula

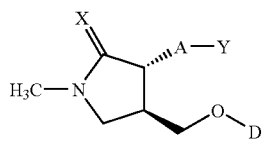

or a pharmaceutically acceptable salt thereof.

8. The compound of claim 1 of the formula

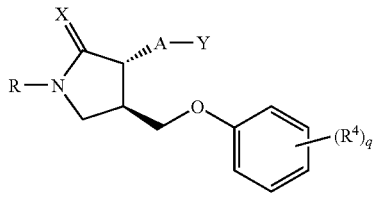

or a pharmaceutically acceptable salt thereof wherein R$^4$ is independently a substituent having from 0 to 10 carbon atoms and from 0 to 5 heteroatoms selected from the group consisting of Cl, F, Br, O, N, and S;

q is 0, 1, 2, 3, or 4; and wherein two R$^4$ moieties may form a ring with two carbon atoms of the phenyl ring.

9. The compound of claim 1 of the formula

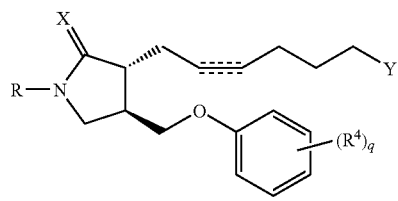

or a pharmaceutically acceptable salt thereof.

10. The compound of claim 1 of the formula

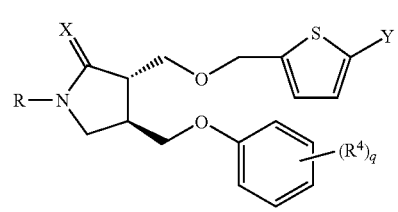

or a pharmaceutically acceptable salt thereof;

wherein R$^4$ is independently a substituent having from 0 to 10 carbon atoms and from 0 to 5 heteroatoms selected from the group consisting of Cl, F, Br, O, N, and S;

q is 0, 1, 2, 3, or 4; and wherein two R$^4$ moieties may form a ring with two carbon atoms of the phenyl ring.

11. A compound of claim 1 of the formula

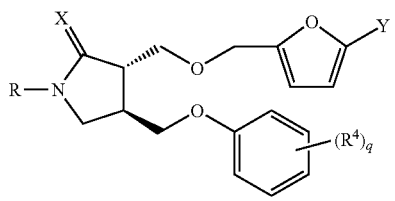

or a pharmaceutically acceptable salt thereof;
 wherein R⁴ is independently a substituent having from 0 to 10 carbon atoms and from 0 to 5 heteroatoms selected from the group consisting of Cl, F, Br, O, N, and S;
 q is 0, 1, 2, 3, or 4; and
 wherein two R⁴ moieties may form a ring with two carbon atoms of the phenyl ring.

12. A compound of claim 1 of the formula

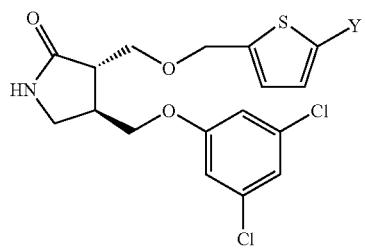

or a pharmaceutically acceptable salt thereof.

13. A method comprising administering a compound according to claim 1 for the treatment of baldness.

* * * * *

UNITED STATES PATENT AND TRADEMARK OFFICE
CERTIFICATE OF CORRECTION

PATENT NO. : 7,705,001 B2  Page 1 of 2
APPLICATION NO. : 12/405684
DATED : April 27, 2010
INVENTOR(S) : David W. Old It is certified that error appears in the above-identified patent and that said Letters Patent is hereby corrected as shown below:

On the Title page, in Item (56), under "Other Publications", column 2, line 7, delete "Am ino" and insert -- Amino --, therefor.

In column 1, line 34, delete "pupilary" and insert -- pupillary --, therefor.

In column 2, line 23, delete "varialoforme," and insert -- varioliforme, --, therefor.

In column 2, line 28, delete "nodose," and insert -- nodosa, --, therefor.

In column 2, line 31, delete "neohropathy," and insert -- nephropathy, --, therefor.

In column 2, line 43, delete "periodonritis," and insert -- periodontitis, --, therefor.

In column 38, line 5, delete "physologicla" and insert -- physiological --, therefor.

In column 38, line 30, delete "betain," and insert -- betaine, --, therefor.

In column 38, line 56, delete "metiparanolol," and insert -- metipranolol, --, therefor.

In column 39, line 7, delete "pilocarbine" and insert -- pilocarpine --, therefor.

In column 39, line 10, delete "chlolinesterase" and insert -- cholinesterase --, therefor.

In column 39, line 15, delete "dextrophan, detromethorphan," and insert -- dextrorphan, dextromethorphan, --, therefor.

In column 39, line 20, delete "nifedimpine," and insert -- nifedipine, --, therefor.

In column 39, line 26, delete "chloprostenol," and insert -- cloprostenol, --, therefor.

In column 39, line 27, delete "chloprostenol," and insert -- cloprostenol, --, therefor.

Signed and Sealed this

Nineteenth Day of October, 2010

David J. Kappos
*Director of the United States Patent and Trademark Office*

In column 39, line 50-51, delete "vasuclar" and insert -- vascular --, therefor.

In column 40, line 25, delete "accosiated" and insert -- associated --, therefor.

In column 40, line 43, delete "pigement" and insert -- pigment --, therefor.

In column 40, line 47, delete "uveitus," and insert -- uveitis, --, therefor.

In column 46, line 2-3, delete "glucouronide," and insert -- glucuronide, --, therefor.

In column 46, line 11, delete "chondroiton" and insert -- chondroitin --, therefor.

In column 46, line 28-29, delete "salsalazine" and insert -- sulfasalazine --, therefor.